United States Patent [19]

Yamatsu et al.

[11] 4,454,126
[45] Jun. 12, 1984

[54] PHOSPHORAMIDE DERIVATIVES AND MEDICINES CONTAINING THE SAME

[75] Inventors: Isao Yamatsu, Ushikumachi; Yuichi Inai, Tokyo; Takeshi Suzuki, Ushikumachi; Shinya Abe, Kukizaki; Masaru Satoh, Sakura; Naosuke Seto, Ichikawa, all of Japan

[73] Assignee: Eisai Co., Ltd., Tokyo, Japan

[21] Appl. No.: 434,454

[22] Filed: Oct. 15, 1982

[30] Foreign Application Priority Data

Oct. 19, 1981 [JP] Japan ................... 56-165669

[51] Int. Cl.³ ............. C07F 9/02; C07F 9/22; A61K 31/66
[52] U.S. Cl. ................ 424/212; 260/403; 424/211; 564/14
[58] Field of Search .......... 564/14; 260/403; 424/211, 212

[56] References Cited

U.S. PATENT DOCUMENTS 3,962,433 6/1976 Worms et al. ............. 424/212
4,182,881 1/1980 Bayless et al. ............. 564/14 X

OTHER PUBLICATIONS

Yamatsu et al., CA 99:53971t (1982).

Primary Examiner—Thomas A. Waltz
Attorney, Agent, or Firm—Flynn, Thiel, Boutell & Tanis

[57] ABSTRACT

Phosphoramide derivatives of the general formula:

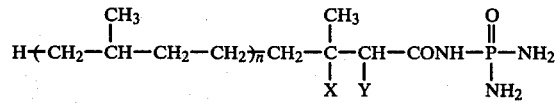

are disclosed wherein X and Y each represents a hydrogen atom or X and Y are removed to form a double bond between the respective adjoining carbon atoms, and n represents an integer of 0 to 2. A process for the preparation of these compounds and pharmaceutical compositions containing these phosphoramide derivatives are also disclosed. The phosphoramide derivatives of the invention are used to treat urethral calculosis and pyelonephritis.

11 Claims, No Drawings

PHOSPHORAMIDE DERIVATIVES AND MEDICINES CONTAINING THE SAME

The present invention relates to phosphoramide derivatives, processes for producing the same and pharmaceutical compositions containing the same. More particularly, the present invention relates to phosphoramide derivatives of the formula:

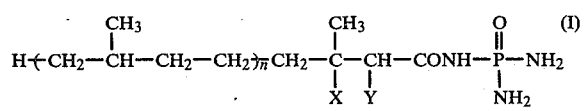

wherein X and Y each represents a hydrogen atom or X and Y together form a valence bond between the two adjacent carbon atoms to which they are respectively attached, and n represents an integer of 0 to 2, processes for producing the same, and pharmaceutical compositions containing the same as an active ingredient for the treatment of urethral calculosis.

Urethral calculosis is presently a difficult-to-treat disease in the field of urology. The term "urethral calculosis" includes calculosis in the renal pelvis, calyx, ureter, bladder, urethra and prostrate.

The urethral calculi may be classified according to the components thereof roughly into the classes of phosphatic stones, oxalate stones, urate stones and cystine stones. Clinically, some of these stones are recognized as being mixtures. It is estimated from statistical data that phosphatic stones, including mixtures thereof, amount to about 40 to 60% of all types of urethral stones. Thus, phosphatic stones are one of the two most common types of urethral stones, the other being oxalate stones.

The causative mechanism of phosphate calculosis is generally as follows: if the urethra becomes infected by a urease-producing bacteria, such as Myxomycetes bacteria, urea in the urine is decomposed into ammonia, which makes the urine alkaline. As a result, insoluble phosphates, such as magnesium ammonium phosphate, are precipitated to form phosphatic stones. Refer to Hideo Takeuchi et al, "Urology Bulletin", 23, (7), 647–651 (1977).

Patients afflicted with phosphatic calculosis caused by such a urethral infection do not recuperate well clinically in comparison with other calculosis patients. Therefore, this type of urethral calculosis has been considered to be highly malignant.

Therapeutic methods for the treatment of phosphatic calculosis now employed clinically may be divided roughly into the following two groups. The first group comprises methods for removing the stones by a surgical operation, and the second group comprises methods for eliminating the urease-producing bacteria, such as Myxomycetes bacteria, by means of a medicine, such as a urethral antibiotic, e.g., ampicillin. However, surgical treatments are of limited effectiveness because the phosphatic stones are brittle and easily broken, and therefore phosphatic stones cannot be removed completely, and, in addition, the phosphatic calculosis condition often recurs. As for the methods of medicinal treatment using urethral antibiotics, it has been recognized generally by clinicians that the effectiveness of the antibiotics is seriously reduced. A reason for this is that the degree to which the bacteria are removed by the antibiotics is insufficient because of the presence of the phosphatic stones.

Further, in view of the appearance of new antibiotic-resistant strains of urease-producing bacteria, microbial substitution and secondary effects of the antibiotics, continuous administration of the antibiotics in large amounts over a long period of time is not desirable. If only an antibiotic is used, the intended treatment cannot be effected sufficiently at present. Under these circumstances, the development of a new therapeutic method has eagerly been desired by clinicians.

Recently, the mechanism of the onset of the above-mentioned phosphatic urethral calculosis has attracted attention. Research has been conducted on hydroxamic acid compounds which specifically inhibit the decomposition, caused by the urease, of urea in urine into ammonia. Further, phosphoramide derivatives, such as N-(diaminophosphinyl)benzamide, have been reported (U.S. Pat. No. 4,182,881). However, clinically acceptable compounds have not yet been developed.

After intensive investigations of various compounds, the inventors have discovered that phosphoramide derivatives of the general formula:

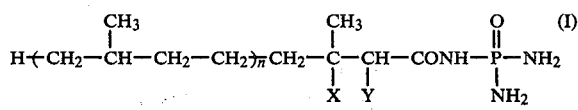

wherein X and Y each represents a hydrogen atom or X and Y together form a valence bond between the two adjacent carbon atoms to which they are respectively attached, and n represents an integer of 0 to 2, have excellent effects as agents for the treatment of urethral calculosis.

More particularly, the inventors have found that phosphoramide derivatives of the above formula (I), which have an isoprenoid chain and a structure different from known compounds, have a strong urease-inhibiting effect, a strong stone formation-inhibiting effect, a high rate of migration into urine and a high degree of safety. Therefore, the invention compounds can be administered continually over a long period of time, and can be used as an excellent agent for the treatment of urethral calculosis, especially phosphatic stones, and pyelonephritis, or as an agent for reducing the incidence or recurrence of these conditions. The present invention has been completed on the basis of these findings.

Accordingly, an object of the present invention is to provide new phosphoramide derivatives useful as an agent for the treatment of urethral calculosis and which are safe for therapeutic use.

Another object of the present invention is to provide processes for producing such new phosphoramide derivatives.

Still another object of the present invention is to provide pharmaceutical compositions for treatment of urethral calculosis or pyelonephritis containing the new phosphoramide derivatives as the active ingredients therein.

The compounds of the present invention have novel structures which have not been disclosed in the known literature. Specific examples of the invention compounds are the following:

N-(diaminophosphinyl)-3-methyl-2-butenamide,
N-(diaminophosphinyl)-3-methylbutanamide, N-(diaminophosphinyl)-3,7-dimethyl-2-octenamide,
N-(diaminophosphinyl)-3,7-dimethyloctanamide,
N-(diaminophosphinyl)-3,7,11-trimethyl-2-dodecenamide, and
N-(diaminophosphinyl)-3,7,11-trimethyldodecanamide.

The processes used for the production of the compounds of the present invention are given below:

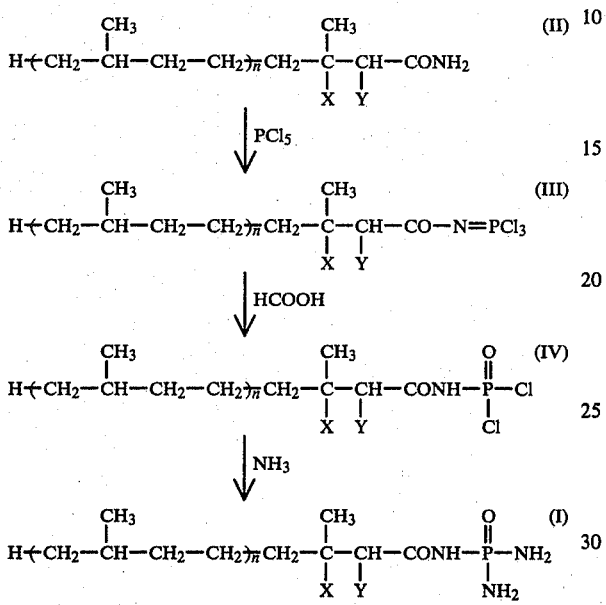

wherein n, X and Y have the same meanings as defined above.

A carboxamide of the above formula (II) is reacted with phosphorus pentachloride to obtain a compound (III), which is then reacted with formic acid to form a phosphoryl chloride of formula (IV), and finally the compound (IV) is reacted with ammonia to obtain the intended compound (I).

The above reactions carried out for obtaining compound (I) from compound (II) can be effected in a solvent suitably selected from inert solvents which do not participate in the reaction. As such solvents, there can be mentioned, for example, carbon tetrachloride, chloroform, diethyl ether and tetrahydrofuran. Preferred results are obtained by controlling the reaction temperature so that it remains within the range of about $-10°$ C. to room temperature in the steps used to obtain (IV) from (II), and a range of about $-20°$ to $20°$ C. in the step of obtaining (I) from (IV).

For further illustrating the effects of the present invention, examples of pharmacological experiments are given below.

As a control compound, N-(diaminophosphinyl)benzamide (U.S. Pat. No. 4,182,881) was employed and compared with the compounds of the present invention.

Test [1] Urease inhibition effects

Urease extracted from Jack beans and then purified and urease produced by *Proteus mirabilis* were used. The molar concentration of the test compound that inhibited 50% of the urease present was determined by the method of Kobashi et al, Biochim. Biophys. Acta, 227, 429–441 (1971), and the method of Okuda et al, Saishin Igaku (The Latest Medical Science) 21(3), 622–627 (1966).

The test compounds were as follows:
Invention Compound A

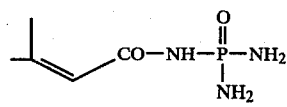

N-(diaminophosphinyl)-3-methyl-2-butenamide
Invention Compound B

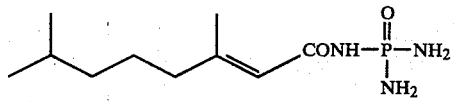

N-(diaminophosphinyl)-3,7-dimethyl-2-octenamide
Invention Compound C

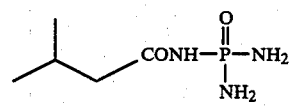

N-(diaminophosphinyl)-3-methylbutanamide
Invention Compound D

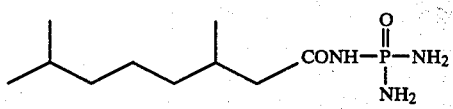

N-(diaminophosphinyl)-3,7-dimethyloctanamide
Control Compound

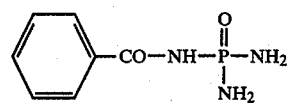

N-(diaminophosphinyl)benzamide
The results are shown in Table 1.

TABLE 1

| | Urease-inhibition effects | | |
|---|---|---|---|
| | 50% Urease inhibition conc. (M) $I_{50}$ | | |
| | Jack bean | *Proteus mirabilis* | |
| Test Compound | urease | Intact cell | Cell free |
| Compound A | $6.3 \times 10^{-7}$ | $1.8 \times 10^{-8}$ | $1.6 \times 10^{-8}$ |
| Compound B | $5.2 \times 10^{-6}$ | $1.5 \times 10^{-8}$ | $1.6 \times 10^{-8}$ |
| Compound C | $1.6 \times 10^{-6}$ | $6.8 \times 10^{-8}$ | $6.1 \times 10^{-8}$ |
| Compound D | $8.7 \times 10^{-7}$ | $1.4 \times 10^{-8}$ | — |
| Control Compound | $6.0 \times 10^{-7}$ | $1.8 \times 10^{-8}$ | $1.3 \times 10^{-8}$ |

It is evident from Table 1 that the compounds of the present invention exhibited strong urease-inhibiting effects.

Test [2] Rate of migration into urine 50 mg/kg of a test compound was administered perorally to S.D. rats weighing around 200 g. The urease-inhibition capacity of urine excreted for 24 hrs. thereafter was measured. The rate of migration into urine of each test compound was determined by the method of Kobashi et al, Yakugaku Zasshi 93(12), 1564–1572 (1973) and J. Biochim. 83, 287–293 (1973).

The results are shown in Table 2.

TABLE 2

| | Rate of migration into urine |
|---|---|
| Test Compound | Rate of migration into urine (%) Average ± S.E. |
| Compound A | 29.6 ± 2.1 |
| Control Compound | 21.0 ± 2.7 |

It is evident from Table 2 that the compound of the present invention exhibited a high rate of migration into urine and was superior to the control compound ($P < 0.05$).

Test [3] Inhibition of the formation of vesical calculi in rats infected with *Proteus mirabilis*:

Female S.D. rats weighing about 200 g were inoculated with *Proteus mirabilis* in their bladders to cause infection. Four days after the inoculation peroral administration of a test compound was begun and the administration was continued for five days. The calculi formed in the bladder in each rat were weighed. The results are shown in Table 3.

TABLE 3

| Test Compound | Dose (mg/kg) per day | Weight of calculi (mg) (Average ± S.E.) | Significant difference |
|---|---|---|---|
| None | — | 34.5 ± 2.6 | |
| Compound A | 50 | 10.9 ± 2.8 | 0.001 |
| | 12.5 | 10.7 ± 3.9 | 0.001 |
| Control Compound | 12.5 | 22.5 ± 4.0 | 0.05 |

It is evident from Table 3 that the compound of the present invention had an excellent effect of inhibiting the formation of calculi and was far superior to the control compound.

Test [4] Acute toxicity

Acute toxicities of test compounds were examined by the peroral administration of the test compounds, suspended in 0.5% carboxymethylcellulose, to male and female S.D. rats (8 weeks old).

The results are shown in Table 4.

TABLE 4

| | Acute toxicity ($LD_{50}$) | |
|---|---|---|
| Test Compound | | $LD_{50}$ mg/kg |
| Compound A | Male | >6,000 |
| | Female | >4,242 |

It was confirmed from Table 4 that compound A, a typical compound of the present invention, had only a very low toxicity and was of quite high safety.

The results of the above pharmacological experiments suggest that the compounds of the present invention have a strong urease-inhibiting effect and a high rate of migration into urine. Therefore, the invention compounds are remarkably effective for inhibiting calculus formation and are useful to treat urethral calculosis conditions, especially urethral phosphatic calculosis. It is even more important that the compounds of the present invention have only a very low toxicity so that they are highly safe to use for the treatment of urethral calculosis, especially urethral phosphatic calculosis, because the continual adminstration of a medicine over a long period of time is required in the treatment of urethral calculosis.

The compounds of the present invention exhibit excellent effects in the treatment of urethral calculosis, especially urethral phosphatic calculosis, when used as the sole treatment agents. However, the invention compounds may also be used in combination with other urethral antibiotics, such as ampicillin, sulfamethoxazole, sulfisomesole, sulfametopyrazin and nitrofurantoin.

It has been said that pyelonephritis caused by infection by urease-producing bacteria, such as Myxomycetes bacteria, becomes clinically serious because of the toxicity of the ammonia formed by the decomposition of the urea contained in urine. The compounds of the present invention are also useful for treatment of pyelonephritis caused by such bacteria. It is also possible in this case to use the compounds of the present invention in combination with the above-mentioned urethral antibiotics.

In the treatment of urethral calculosis and pyelonephritis with the compounds of the present invention, the invention compounds can be administered perorally or parenterally, for example, by intramuscular, subcutaneous or intravenous injection or by suppositories. The dosage for human treatment varies depending on the condition of the patient, and is generally in the range of from 20 to 3,000 mg/day/adult, preferably 500 to 1,500 mg/day/adult.

The compounds of the present invention are used in the form of tablets, granules, powders, capsules, injectable solutions or suppositories prepared by methods customarily employed in the technical field of pharmaceutical composition preparation.

In the preparation of solid products for peroral administration, an excipient, and if necessary, a binder, a disintegration aid, a lubricant, a coloring agent and a corrigent are added to the compound, and then the resulting mixture is shaped into tablets, coated tablets, granules, powders or capsules.

As the excipient there can be used, for example, lactose, corn starch, white sugar, glucose, sorbitol or crystalline cellulose. As the binder there can be used, for example, polyvinyl alcohol, polyvinyl ether, ethylcellulose, methylcellulose, acacia, tragacanth, gelatin, shellac, hydroxypropylcellulose, hydroxypropylstarch, polyvinylpyrrolidone, white sugar or sorbitol. As the disintegration aid there can be used, for example, starch, agar, gelatin powder, crystalline cellulose, calcium carbonate, sodium hydrogencarbonate, calcium citrate, dextrin or pectin. As the lubricant there can be used, for example, magnesium stearate, talc, polyethylene glycol, silica or hardened vegetable oils. As the coloring agent there can be used any known coloring agent accepted as a medicine additive. As the corrigent there can be used cocoa powder, menthol, aromatic powder, peppermint oil, borneol or cinnamon powder. These tablets and granules may be coated, if necessary, with sugar, gelatin or the like.

In the preparation of a liquid product for peroral administration, a corrigent, buffer agent, stabilizer, etc. are added, if necessary, to the compound and then the mixture is dissolved in a syrup by a conventional method.

In the preparation of injectable solutions, a pH adjustor, buffer agent, suspending agent, solubilizer, stabilizer, isotonizer, preservative, and the like are added, if necessary, to the compound and the mixture is formed into a solution for subcutaneous, intramuscular or intravenous injection.

As suspending agents, there can be mentioned, for example, methylcellulose, polysorbate 80, hydroxyethylcellulose, acacia, tragacanth powder, sodium carboxymethylcellulose and polyoxyethylene sorbitan monolaurate. As solubilizers, there can be mentioned, for example, polyoxyethylene hardened castor oil, polysorbate 80, nicotinamide, polyoxyethylene sorbitan monolaurate, macrogol and ethyl esters of castor oil fatty acids. As the stabilizers, there can be mentioned, for example, sodium sulfite, sodium metasulfite and ethers. As the preservatives, there can be mentioned, for example, methyl p-hydroxybenzoate, ethyl p-hydroxybenzoate, sorbic acid, phenol, cresol and chlorocresol.

The following examples further illustrate the present invention, but do not limit the scope of the invention.

PREPARATION EXAMPLE 1

N-(Diaminophosphinyl)-3-methyl-2-butenamide 10 g of 3-methyl-2-butenamide was dissolved in 350 ml of anhydrous tetrahydrofuran. 20 g of phosphorus pentachloride was added to the resulting solution under cooling to $-10°$ C. and the mixture was stirred for 30 minutes. Then, 4.6 g of 99% formic acid was added dropwise to the mixture at $-10°$ C. and the entire mixture was stirred at 20° C. for 30 minutes. The reaction liquid was then subjected to suction filtration. Gaseous ammonia was introduced into the filtrate under cooling to $-20°$ C. The temperature of the mixture was elevated to room temperature and the mixture was stirred for 30 minutes. The resulting crystals were filtered out. After extraction with 100 ml of warm methanol twice, the extract was cooled to $-20°$ C. and the crystals thus formed were filtered out. After recrystallization from 100 ml of methanol, 5.5 g of the intended product compound was obtained. The characteristics of the product were as follows:

(1) Melting point: 180° C. (decomposition)

| (2) Elementary analysis as $C_5H_{12}N_3O_2P.\frac{1}{2}H_2O$: | | | | |
|---|---|---|---|---|
| | C | H | N | P |
| Calculated (%) | 32.26 | 6.99 | 22.58 | 16.64 |
| Found (%) | 32.16 | 6.87 | 22.85 | 16.47 |

(3) I.R. (cm$^{-1}$):

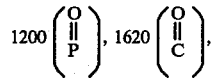

1660 (C=C), 3100~3400 (NH)

(4) N.M.R. (δ value, DMSO): 2.80 (3H, doublet), 2.10 (3H, doublet), 4.04 (4H, singlet), 5.82 (1H, singlet), 8.85 (1H, singlet).

PREPARATION EXAMPLE 2

N-(Diaminophosphinyl)-3-methylbutanamide 14 g of 3-methylbutanamide was dissolved in 300 ml of carbon tetrachloride. 14 g of phosphorus pentachloride was added to the resulting solution at room temperature and the mixture was stirred for 30 minutes. 3.1 g of 99% formic acid was added dropwise to the mixture and the entire mixture was stirred at room temperature for 30 minutes. Then, gaseous ammonia was introduced therein under cooling to $-20°$ C. The mixture was warmed to room temperature and was stirred at room temperature for 30 minutes. The resulting crystals were filtered out and extracted with 100 ml of methanol while they were kept warm. The extract was concentrated and recrystallized from methanol to obtain 8 g of the intended product compound, which had the following characteristics:

(1) Melting point: 170° C. (decomposition

| (2) Elementary analysis as $C_5H_{14}N_3O_2P.\frac{1}{2}H_2O$: | | | | |
|---|---|---|---|---|
| | C | H | N | P |
| Calculated (%) | 31.92 | 8.04 | 22.33 | 16.46 |
| Found (%) | 31.77 | 8.16 | 22.51 | 16.25 |

(3) I.R. (cm$^{-1}$):

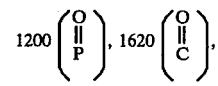

3100~3400 (NH)

(4) N.M.R. (δ value, DMSO): 0.80~0.88 (6H, doublet), 1.80~1.94 (1H, multiplet), 1.98~2.00 (2H, doublet), 3.90 (4H, singlet), 8.80 (1H, singlet).

PREPARATION EXAMPLE 3

N-(Diaminophosphinyl)-3,7-dimethyl-2-octenamide 20 g of 3,7-dimethyl-2-octenamide was dissolved in 600 ml of anhydrous tetrahydrofuran. 24.6 g of phosphorus pentachloride was added to the resulting solution under cooling to $-10°$ C. and the mixture was stirred for 30 minutes. 5.4 g of 99% formic acid was added dropwise to the mixture and the mixture was stirred at room temperature for 30 minutes. Then, gaseous ammonia was introduced therein under cooling to $-20°$ C. The mixture was warmed to room temperature and was stirred at room temperature for 30 minutes. The reaction liquid was subjected to filtration and the filtrate was concentrated. After recrystallization from 100 ml of methanol, the intended product compound was obtained. The product has the following characteristics:

(1) Melting point: 159° C.

| (2) Elementary analysis as $C_{10}H_{22}N_3O_2P.\frac{1}{2}H_2O$: | | | | |
|---|---|---|---|---|
| | C | H | N | P |
| Calculated (%) | 46.86 | 9.05 | 16.40 | 12.08 |
| Found (%) | 46.70 | 9.17 | 16.61 | 12.01 |

(3) I.R. (cm$^{-1}$): 1200

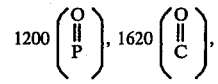

1660 (C=C), 3100~3400 (NH)

(4) N.M.R. (δ value, DMSO): 0.84~9.90 (6H, doublet), 1.00~2.00 (7H, multiplet), 2.08 (3H, singlet), 3.96 (4H, singlet), 5.76 (1H, singlet), 8.76 (1H, singlet).

PREPARATION EXAMPLE 4

N-(Diaminophosphinyl)-3,7-dimethyloctanamide 8 g of 3,7-dimethyloctanamide was dissolved in 100 ml of carbon tetrachloride. 9.7 g of phosphorus pentachloride was added to the resulting solution at room temperature and the mixture was stirred for 30 minutes. Then, gaseous ammonia was introduced therein under cooling to −20° C. The temperature of the mixture was elevated to room temperature and the mixture was stirred at room temperature for 30 minutes. The resulting crystals were filtered out. After the extraction with 100 ml of warm methanol, the concentrated residue was recrystallized from 30 ml of methanol to obtain 3.9 g of the intended product compound.

(1) Melting point: 155° C.

(2) Elementary analysis as $C_{10}H_{24}N_3O_2P \cdot \frac{1}{2}H_2O$:

|  | C | H | N | P |
| --- | --- | --- | --- | --- |
| Calculated (%) | 46.50 | 9.76 | 16.27 | 11.99 |
| Found (%) | 46.35 | 9.87 | 16.42 | 11.77 |

(3) I.R. (cm$^{-1}$):

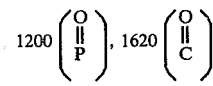

3100~3400 (NH)

(4) N.M.R. (δ value, DMSO): 0.80~0.86 (9H, doublet), 1.00~2.20 (10H, multiplet), 3.90 (4H, singlet), 8.90 (1H, singlet).

PREPARATION EXAMPLE 5

N-(Diaminophosphinyl)-3,7,11-trimethyl-2-dodecenamide 20 g of 3,7,11-trimethyl-2-dodecenamide was dissolved in 300 ml of anhydrous tetrahydrofuran. 17.4 g of phosphorus pentachloride was added to the resulting solution under cooling to −10° C. and the mixture was stirred for 30 minutes. 3.8 g of 99% formic acid was added dropwise to the mixture and the mixture was stirred at room temperature for 30 minutes. Then, gaseous ammonia was introduced therein under cooling to −20° C. The temperature of the mixture was then elevated to room temperature and the mixture was stirred at room temperature for 30 minutes. The reaction liquid was filtered and the filtrate was concentrated. The residue was recrystallized from 300 ml of methanol to obtain 5.0 g of the intended product compound.

(1) Melting point: 134° C.

(2) Elementary analysis as $C_{15}H_{32}N_3O_2P \cdot \frac{1}{2}H_2O$:

|  | C | H | N | P |
| --- | --- | --- | --- | --- |
| Calculated (%) | 55.19 | 10.19 | 12.87 | 9.49 |
| Found (%) | 55.01 | 10.30 | 12.99 | 9.28 |

(3) I.R. (cm$^{-1}$):

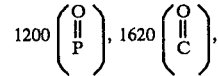

1660 (C=C), 3100~3400 (NH)

(4) N.M.R. (δ value, DMSO): 0.82~0.88 (9H, doublet), 1.00~2.04 (14H, multiplet), 2.08 (3H, singlet), 3.98 (4H, singlet), 5.80 (1H, singlet), 8.74 (1H, singlet).

PREPARATION EXAMPLE 6

N-(Diaminophosphinyl)-3,7,11-trimethyldodecanamide 8.5 g of 3,7,11-trimethyldodecanamide was dissolved in 100 ml of carbon tetrachloride. 7.3 g of phosphorus pentachloride was added to the resulting solution at room temperature and the mixture was stirred for 30 minutes. 1.6 g of 99% formic acid was added dropwise to the mixture and the mixture was stirred for 30 minutes. Then, gaseous ammonia was introduced therein under cooling to −20° C. The temperature was elevated to room temperature and the mixture was stirred at room temperature for 30 minutes. The reaction liquid was filtered and the filtrate was concentrated. The residue was recrystallized from methanol to obtain 4.0 g of the intended product compound.

(1) Melting point: 132° C.

(2) Elementary analysis as $C_{15}H_{34}N_3O_2P \cdot \frac{1}{2}H_2O$:

|  | C | H | N | P |
| --- | --- | --- | --- | --- |
| Calculated (%) | 54.86 | 10.74 | 12.79 | 9.43 |
| Found (%) | 54.62 | 10.86 | 12.90 | 9.22 |

(3) I.R. (cm$^{-1}$):

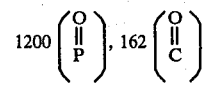

3100~3400 (NH)

(4) N.M.R. (δ value, DMSO): 0.80~0.86 (12H, doublet), 1.00~2.20 (17H, multiplet), 3.90 (4H, singlet), 8.82 (1H, singlet).

The embodiments of the invention in which an exclusive property or privilege is claimed are defined as follows:

1. A compound having the formula:

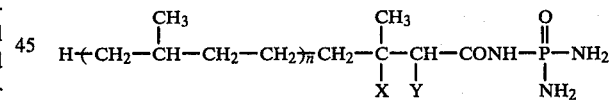

wherein X and Y each represents hydrogen or X and Y together form a valence bond between the two adjacent carbon atoms to which they are respectively attached, and n represents an integer of 0 to 2.

2. A compound according to claim 1 which is N-(diaminphosphinyl)-3-methyl-2-butenamide.

3. A compound according to claim 1 which is N-(diaminophosphinyl)-3-methyl-butanamide.

4. A compound according to claim 1 which is N-(diaminophosphinyl)-3,7-dimethyl-2-octenamide.

5. A compound according to claim 1 which is N-(diaminophosphinyl)-3,7-dimethyl octanamide.

6. A compound according to claim 1 which is N-(diaminophosphinyl)-3,7,11-trimethyl-2-dodecenamide.

7. A compound according to claim 1 which is N-(diaminophosphinyl)-3,7,11-trimethyldodecanamide.

8. A pharmaceutical composition for the treatment of urethral calculosis comprising an effective amount of a phosphoramide derivative of the formula:

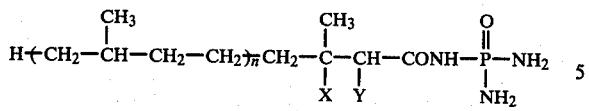

wherein X and Y each represents hydrogen or X and Y together form a double bond between the two adjacent carbon atoms to which they are respectively attached, and n represents an integer of 0 to 2, as an active ingredient, and a pharmaceutically acceptable carrier.

9. A pharmaceutical composition for the treatment of pyelonephritis caused by a urethral infection of urease-producing bacteria comprising an effective amount of a phosphoramide derivative of the formula:

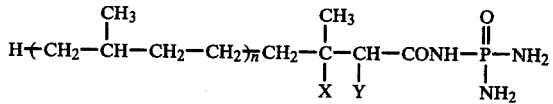

wherein X and Y each represents hydrogen or X and Y together form a double bond between the two adjacent carbon atoms to which they are respectively attached, and n represents an integer of 0 to 2, as an active ingredient, and a pharmaceutically acceptable carrier.

10. A method of treating a patient afflicted with urethral calculosis which comprises administering to said patient a therapeutically effective amount of a pharmaceutical composition as claimed in claim 8.

11. A method of treating a patient afflicted with pyelonephritis which comprises administering to said patient a therapeutically effective amount of a pharmaceutical composition as claimed in claim 9.

* * * * *